Figure 2:
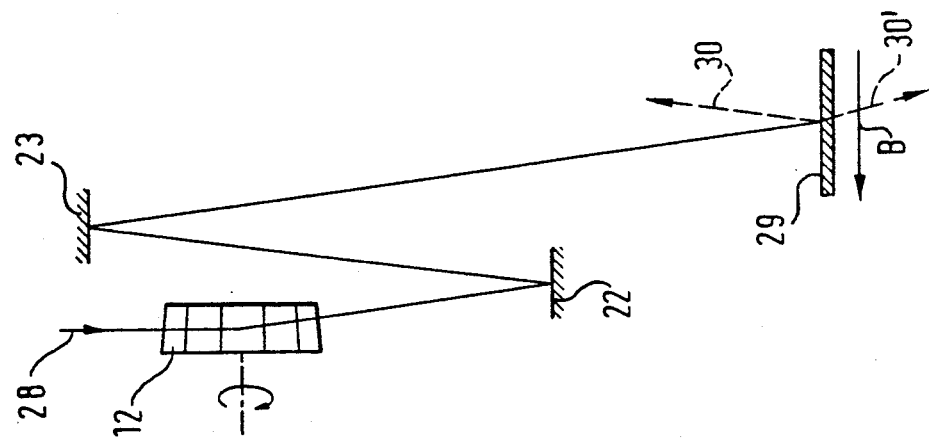

United States Patent [19]

Weber

[11] Patent Number: 5,079,434
[45] Date of Patent: Jan. 7, 1992

[54] OPTICAL SCANNING APPARTAUS FOR SEEKING FAULTS ON MOVING MATERIAL WEBS

[75] Inventor: Klaus Weber, Königsbronn, Fed. Rep. of Germany

[73] Assignee: Erwin Sick GmbH Optik-Elektronik, Waldkirch, Fed. Rep. of Germany

[21] Appl. No.: 560,954

[22] Filed: Aug. 1, 1990

[30] Foreign Application Priority Data

Aug. 2, 1989 [DE] Fed. Rep. of Germany ....... 3925614

[51] Int. Cl.$^5$ .......................................... G01N 21/88
[52] U.S. Cl. ..................................... 250/572; 356/431
[58] Field of Search ............... 250/562, 563, 572, 234, 250/235, 236; 356/430, 431, 237, 238

[56] References Cited

U.S. PATENT DOCUMENTS

| 4,528,455 | 7/1985 | Loose | 250/572 |
| 4,725,139 | 2/1988 | Hack et al. | 250/572 |
| 4,797,558 | 1/1989 | West | 250/236 |

Primary Examiner—David C. Nelms
Assistant Examiner—K. Shami
Attorney, Agent, or Firm—Townsend and Townsend

[57] ABSTRACT

The invention relates to an optical scanning apparatus for the seeking of faults on throughmoving material webs (29) and comprises at least one light source, a mirror wheel (12) arranged in a housing (13) which periodically deflects a light beam produced from the light source in order to generate a scanning beam with which the material web (29) can be scanned transverse to its direction of through-movement (B) along a scanning line (21). A light deflecting device (16) is provided in the housing (13), is arranged after the mirror wheel (12) and brings about a multiple folding of the scanning beam path out of the plane of the fan of scanning beams. The mirror wheel (12) is arranged in the housing (13) with its axis of rotation (14) above one end of the scanning line (21'), with the housing with the optical components (25, 16) arranged therein forming a main scanning module (10). An auxiliary scanning module (11) with a build-on housing (17) can be mounted on the housing (13) of the main scanning module (10) at the side associated with the mirror wheel (12), with a second light source and a second light deflecting means (19) being provided in the build-on housing. In this arrangement the optical components (19, 25) of the auxiliary module (11) are arranged essentially in mirror symmetry to the optical components (16, 25) of the main module. (FIG. 3)

10 Claims, 3 Drawing Sheets

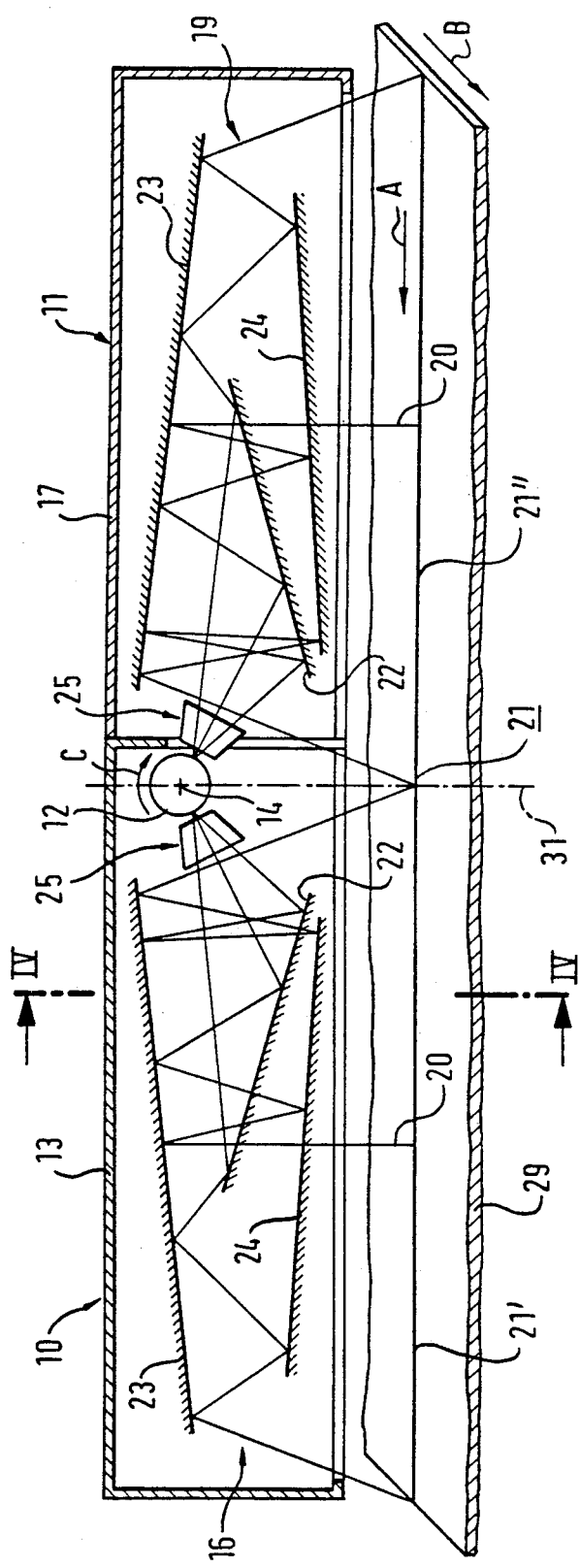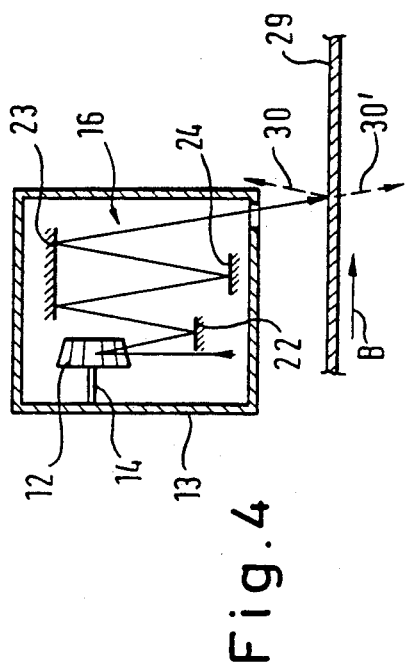

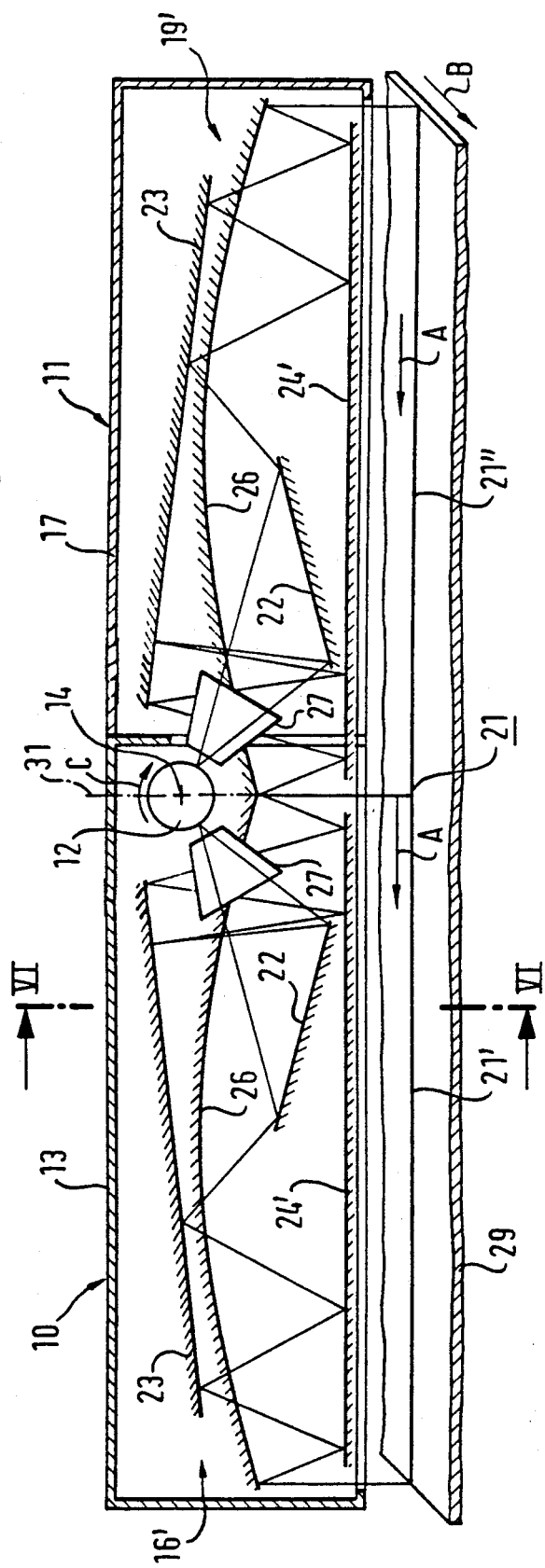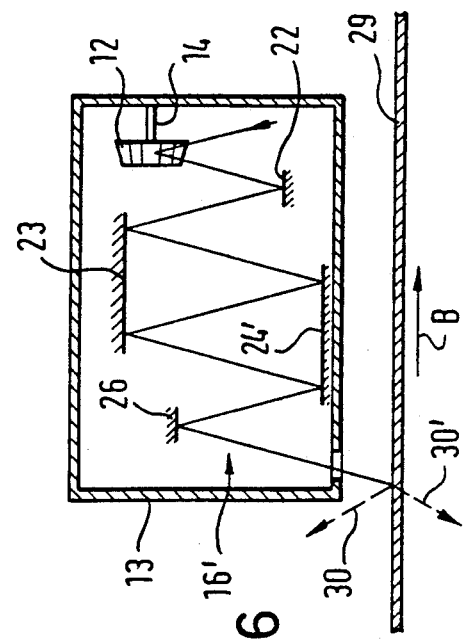

OPTICAL SCANNING APPARTAUS FOR SEEKING FAULTS ON MOVING MATERIAL WEBS

The present invention relates to an optical scanning apparatus for seeking faults on moving material webs comprising at least one light source; a mirror wheel arranged in a housing which periodically deflects a light beam produced by the light source to generate a scanning beam with which the material web can be scanned transverse to its direction of through-movement along a scanning line; and at least one light deflecting device arranged after the mirror wheel which brings about a multiple folding of the scanning beam path out of the plane of the fan of the scanning beams.

Such optical scanning apparatuses have different scanning widths depending on the particular width of the material web to be investigated. The scanning widths lie typically between approximately 100 mm and 2000 mm. The larger the required scanning width the greater is the spacing of the mirror wheel, which represents the starting point of the fan of scanning beams, from the scanning line, i.e. from the material web to be scanned. Thus the constructional height of the optical scanning apparatus is also increased. The large constructional height is disadvantageous not only as a consequence of the large space requirement, but also with regard to the mechanical stability of the construction of the scanning apparatus. Vibrations of the housing can in particular have disadvantageous effects.

In order to reduce the constructional height which is determined by the scanning width, i.e. by the length of the scanning line, the scanning beam path of the scanning apparatus has been folded with the aid of one or more plane deflecting mirrors, with the folding using several deflecting mirrors taking place out of the plane of the fan of the scanning beams.

If material webs with widths of above 2000 mm are to be examined for faults, such as for example in the manufacture of paper, in the manufacture of technical fabrics, with non-woven material and in the manufacture of carpets, several optical scanning devices, in particular scanning devices which operate with lasers, are arranged in series in order to achieve an overall scanning width of up to 5000 mm.

A fault seeking apparatus for broad material webs is already known from DE-PS 31 25 187 in which a plurality of individual scanning devices are arranged in a common housing, with the scanning lines merging into one another in order to achieve a scanning width of for example 5000 mm.

The individual scanning apparatuses thus each have a mirror wheel, and a light deflecting device in which the last deflecting mirror is formed as a concave mirror strip in order to generate a telecentric scanning beam. As the individual scanning devices each operate in autocollimation they are decoupled at the receiver side so that the mirror wheels can run asynchronously.

Another scanning apparatus is known from U.S. Pat. No. 4,260,899 in which the complete individual scanning devices are arranged in series in order to achieve the required scanning width. The light which emerges from the scanning line on the object to be investigated is thereby passed to a common receiver which is formed by a light conducting rod with an associated photomultiplier. It is thus necessary that the individual scanning devices which generate the scanning light beads run along the scanning line one after the other, so that a series scan is realised.

With a series scan of this kind the individual mirror wheels must be electrically synchronously driven. In addition, at the transition points of the individual scanning lines, the scanning light bead which is handing over must be switched out and the scanning light bead of the subsequent individual scanning device which is taking over must be switched on.

Figure 1:
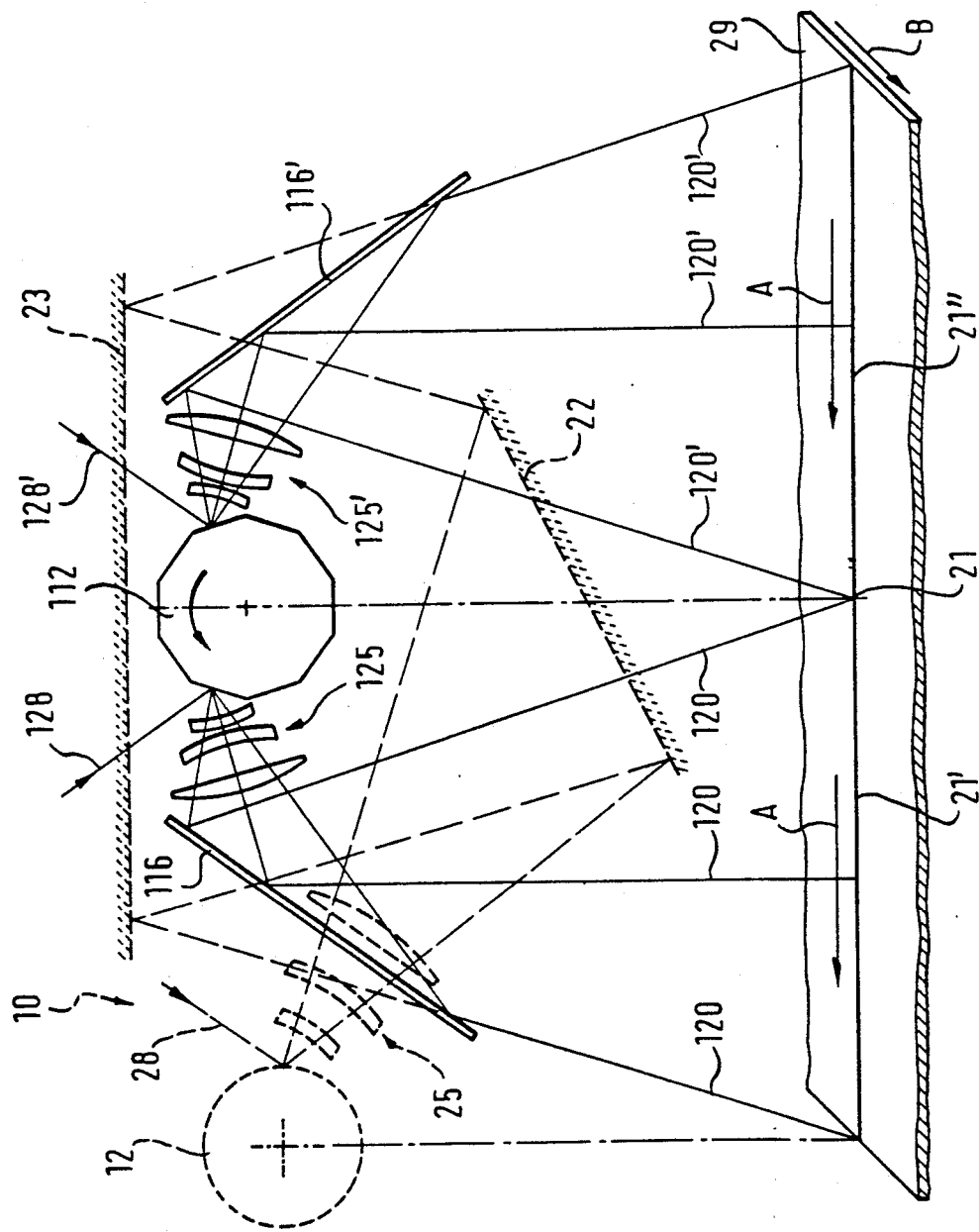

An optical scanning apparatus is known from DE-PS 36 00 578 which, as shown in FIG. 1 of the enclosed drawing, has a mirror wheel 112 which is simultaneously illuminated by two laser light beams 128, 128'. Two scanning objectives 125, 125' which generate divergent scanning beams are arranged after the mirror wheel 112.

A deflecting mirror 116, 116' is provided in each of the two scanning beam paths and brings about a folding of the corresponding scanning beam path in the plane of the fan of the scanning beams. The scanning light bead which is generated by the respective scanning beams on the surface of the material web 29 scans this material web along the scanning line 21 which is composed of the scanning line halves 21', 21".

The direction of the incident laser light beams 128, 128', the number of facets of the mirror wheel 112 and the arrangement of the two scanning objectives 125, 125' with the deflecting mirrors 116, 116' associated therewith is selected such that the scanning light beam 120, 120' run through the scanning line halves 21', 21" associated with them, one after the other timewise, so that a "series scan" is brought about.

The series, synchronous scanning of the material web 29 makes it possible to provide a common receiver for both scanning beam paths with the receiver receiving light emerging from the scanning line 21.

An apparatus is known from the Japanese laying open print 58-105 117 which corresponds to the known scanning apparatus described with reference to FIG. 1. However there the mirror wheel is so laid out that with corresponding illumination with laser light beams the scanning light beams of the two scanning beam paths carry out their scanning movement synchronously timewise and in phase, i.e. in "parallel" timewise.

Through this parallel scanning a scanning speed is achieved in the known scanning apparatus, which is intended for the printing of written documents, which is almost doubled for the same mirror wheel speed and the same number of facets when compared with the apparatus of DE-PS 36 00 578.

The object of the present invention is to provide an optical scanning apparatus of the initially named kind which is able to satisfy the requirements placed on laser scanners for the inspection of through-running material webs of different scanning widths, the requirement for a constructional height which is as low as possible, the requirements for divergent or telecentric scanning systems and finally also the requirement to be able to use different receivers while keeping the range of types required for the product line as low as possible.

This object is satisfied in accordance with the invention in that the mirror wheel is arranged in the housing with its axis of rotation over one end of the scanning line, with the housing with the optical components arranged therein forms a main scanning module; and in that an auxiliary scanning module with a build-on housing can be mounted on the housing of the main scanning module at the side associated with the mirror wheel, with a second light source and a second light deflecting device being provided in the auxiliary scanning module, wherein the optical components of the additional module are arranged essentially mirror-symmetrically to the optical components of the main module with reference to the mirror wheel, so that the end of the scanning line of the main module preferably coincides, somewhat overlapped, with the start of the scanning line of the auxiliary module.

Through the arrangement of the mirror wheel in accordance with the invention, and through the mirror symmetrical arrangement of the light source and of light deflecting devices which bring about a multiple folding of the fan of scanning beams out of the plane of the fan, a modular system for optical scanning apparatus can be provided with single and double scanning functions, in which the main module represents a fully operable optical scanning apparatus with single scanning which ensures a low constructional height, even with comparatively large scanning widths, and simultaneously ensures a simple construction of the apparatus.

Through the simple building on of an auxiliary module the optical components of which are built-up mirror-symmetrically relative to the optical components of the main module, but which uses the mirror wheel of the main module, the scanning width of the scanning apparatus can be doubled in simple manner without increasing the constructional height of the scanning apparatus. At the same time the use of a common mirror wheel ensures that the scanning beams of the main module and of the auxiliary module are necessarily synchronised with one another.

Moreover, the mirror symmetrical construction has the advantage that the same optical components can be used both for the main module and also for the auxiliary module. Both the light source and also the light deflecting devices can thus be manufactured from the same components, whereby the number of the different individual optical components can be reduced, since, for example, the light deflecting device of the main module can be built up from the same mirrors as the light deflecting device of the auxiliary module.

Thus the construction of the optical scanning apparatus in accordance with the invention makes it possible to simplify a production line. Should, for example, inspection devices be made available for the following series of large material widths 1600 mm, 2000 mm, 2500 mm, 3200 mm, 4000 mm and 5000 mm then a main module is produced for each of the scanning widths 1600 mm, 2000 mm and 2500 mm. The scanning widths of 3200 mm, 4000 mm and 5000 mm are then realised in that these main modules are combined with their mating auxiliary modules. Thus with three sizes of housing and three sets of deflecting mirrors one is able to provide six inspection widths.

A further advantage of the essentially mirror symmetrical construction of the main and auxiliary modules lies in the fact that in addition to the identical optical components their mechanical mounts in the corresponding housings can also be made substantially identical.

In a layout of the invention provision is made that the second light deflecting device of the auxiliary module is preferably so arranged that the scanning line generated by the corresponding scanning light beam is displaced parallel to the scanning direction A relative to the scanning line generated by the main module, when the auxiliary module is connected with the main module, with the two scanning lines overlapping one another in the scanning direction A.

Through this arrangement one ensures that a photoreceiver arrangement which is associated with the optical scanning device with double scanning and which receives light reflected or transmitted from the scanning line of the material web can be built-up in extremely simple manner from two photoreceivers which are then associated with corresponding scanning line halves. The photoreceiver arrangements can then either operate with a light conducting rod or in accordance with the principle of pupil imaging.

In another layout of the invention provision is made that the light deflecting device of the auxiliary module is so arranged that the scanning line generated from the corresponding scanning light beam is aligned with the scanning line generated by the main module, when the auxiliary module is connected with the main module. In this way a photoreceiver arrangement with a common light conducting rod and photoreceiver for the two scanning line halves can be used in a simple manner.

In order to further reduce the number of the different components that are used provision is made in accordance with another embodiment of the invention, that the light deflecting device includes plane mirrors of which at least some bring about a double-folding of the scanning beam path. In this way the adjustment of the scanning beam paths is also simplified.

In the embodiments with divergent scanning fans a scanning objective is in each case arranged after the mirror wheel and in front of the light deflecting means in order to generate a fault-free scanning light bead over the entire scanning line. If the objective thereby additionally satisfies the requirement that the position of the scanning beam is proportional to the angle $\theta$ of the incident light beam, i.e., with the focal width F of the objective, amounts to $F \times \theta$ as seen from the optical axis, then the same paths are followed during the scan in the same times. Objectives which make such distorsion-free scanning possible are also called $F\theta$ objectives.

Another embodiment of the invention is characterized in that the last folding of the respective scanning beam path is brought about by a strip-like concave mirror at the focal point of which the center of rotation of the fan beam is arranged, which lies directly behind the respectively effective facet of the mirror wheel, so that a telecentric scanning beam path is generated.

In a further embodiment a correction lens group is provided in front of the respective light deflecting device of the telecentric scanning apparatus. This correction lens group forms, together with the concave mirror, a corrected telecentric scanning system.

In order to ensure a series scan of the scanning line, which is of advantage when the scanning line halves are aligned with one another and when a common photoreceiver arrangement is to be used for both scanning line halves, provision is made in the embodiment of the invention that the mirror wheel is so formed and is so illuminated by the two light sources with connected together scanning modules that the two scanning beams sequentially scan the scanning line.

In order to increase the scanning speed or to reduce the speed of rotation of the mirror wheel for a given speed of advance of the material web to be monitored, provision is made, in accordance with a further embodiment of the invention, that the mirror wheel is so formed and is so illuminated by the two light sources with assembled scanning modules that the two scanning beams simultaneously scan the scanning line. It is then however necessary to operate with two separate receiving systems for most inspection tasks.

The invention will now be described in more detail in the following by way of example and with reference to the drawings in which are shows:

FIG. 1 a schematic representation of a known optical scanning apparatus with double-scanning which is shown in full lines overlaid with a schematic illustration of a single scanning apparatus in accordance with the invention which is shown in broken lines, FIG. 2 a schematic sideview of the optical scanning apparatus in accordance with the invention as shown in FIG. 1, FIG. 3 a divergent optical scanning apparatus with double-scanning in accordance with the invention, FIG. 4 a section essentially on the line IV—IV in FIG. 3, FIG. 5 a schematic representation of a telecentric optical scanning apparatus with double-scanning in accordance with the invention, and FIG. 6 a schematic section essentially on the line VI—VI in FIG. 5.

In the various figures of the drawings components which correspond with one another are designated with the same reference numerals.

The scanning apparatus of the invention shown in broken lines in FIG. 1 comprises a main scanning module 10 which has a mirror wheel 12. The mirror wheel 12 is illuminated by a laser light beam 28 which is generated from a non-illustrated laser light source. The laser light beam 28 which is periodically deflected by the mirror wheel 12 passes via an optical scanning system 25 which is formed as an F-θ objective onto a first plane mirror 22 and from there via a second plane mirror 23 onto the surface of a material web 29 to be monitored when a scanning light bead is generated.

As a consequence of the rotation of the mirror wheel the scanning light beam is periodically displaced so that the scanning light bead which it generates brings about a scan along the scanning line 21 in the direction of the arrow A. Through the simultaneous displacement of the material web 29 in the direction of the arrow B it is possible to achieve a substantially gap-free monitoring of the material web 29.

The fan of scanning beams is folded twice out of its plane by the two plane mirrors 22, 23 which can be seen particularly clearly in FIG. 2.

In this manner a scanning width can be obtained with a single fan of scanning beams which is the same as the scanning width of the optical scanning apparatus with double scanning shown in full lines in FIG. 1. Moreover, the constructional height of the scanning apparatus of the invention, i.e. essentially the distance of the second plane mirror 23 from the material web 29 is almost precisely as large as the constructional height of the known scanning apparatus, with the construction of the apparatus of the invention however being substantially simplified since only one scanning objective 25 and one laser light source are required.

The detection of the scanning light beam 30 reflected from the material web or of the scanning light beam 30' which passes through the material web 29 takes place in the customary manner, for example by means of a light conducting rod, or also by means of a photoreceiver arrangement operating in accordance with the principle of pupil imaging, and is thus not illustrated.

The optical scanning apparatus of the invention shown in FIG. 3 comprises a main module 10 and an auxiliary module 11. The main module 10 thereby has a housing 13 in which there is arranged a mirror wheel 12 which rotates in operation in the direction of the arrow C. The mirror wheel 12 is illuminated by a non-illustrated light source, in particular by a laser and deflects the incident light beam periodically onto a scanning objective 25 which is formed as a Fθ objective in order to generate a divergent fan of scanning beams. The scanning light beam which leaves the scanning objective 25 is multiply deflected by a first light deflecting device 16 which is built-up from three plane mirrors 22, 23, 24 each bringing with the plane mirrors 22, 23, 24 each bringing about a folding of the scanning beam fan out of its plane, and at the same time substantially parallel to its plane.

The folding of the scanning beam fan essentially parallel to its plane is particularly clear from the middle ray 20 of the scanning beam fan which coincides with the optical axis of the scanning objective 25.

A built-on housing 17 of the auxiliary module 11 is attached to the housing 13 of the main module 10. In the built-on housing 17 there is arranged a second light deflecting device 19 which is likewise built-up of plane mirrors 22, 23, 24, with the arrangement of the second light deflecting device 19 being of mirror symmetry to the arrangement of the first light deflecting device 16, and indeed in relation to the plane of symmetry 31 which extends perpendicular to the scanning lines 21' and 21" through the axis of rotation 14 of the mirror wheel 12.

Moreover, a second scanning objective 25 is arranged in the built-on housing 17 of the auxiliary module 11 which is identical with the first scanning objective 25 and which is likewise arranged in mirror symmetry to the first scanning objective 25 with respect to the plans of symmetry 31.

In order to displace the scanning line 21" generated by the scanning beam of the auxiliary module 11 on the surface of the material web 29 parallel to the scanning line 21' which is generated by the scanning beam of the main module 10, one of the deflecting mirror strips can for example be executed as a roof-shaped mirror strip.

As can be seen from FIG. 4 the fan of the scanning beams is folded out of its plane four times, with the second plane mirror 23 folding the fan of scanning beams twice.

The photoreceiver arrangements for the scanning beams 30 or 30' reflected or transmitted from the material web are not shown.

Through the parallel displacement of the scanning beam lines 21', 21" it is possible to provide a respective photoreceiver for each half of the material web 29 so that the scanning beams of the main and auxiliary modules 10 and 11 respectively can scan the material web 29 synchronously and in phase, i.e. in parallel timewise, whereby a double speed of scanning is achieved which is of advantage, in particular with material webs which run at high speed.

The timewise parallel scanning is thereby achieved through a corresponding layout of the mirror wheel 12.

A further optical scanning apparatus in accordance with the invention will be described with respect to FIGS. 5 and 6 and is again put together from a main module 10 and as an auxiliary module 11.

In the housings 13 and 17 of the main module 10 and auxiliary module 11 respectively there are provided first and second light deflecting devices 16' and 19' and in each case a correction lens group 27. The correction lens groups 27 thereby form, together with a strip-like concave mirror 26 of the first and second light deflecting devices 16' and 19' respectively, a corrected scanning system which generates a telecentric scanning beam path. The scanning light beams which are incident onto the material web 29 are thus parallel to one another.

The scanning lines 21' and 21" generated by the scanning light beams of FIGS. 5 and 6 are shown aligned with one another which is useful for series scanning. A parallel double-scanner can however also be built-up here by the introduction of a roof mirror strip.

As can be seen particularly clearly in FIG. 6 the fan of scanning light beams is in each case folded twice by the plane mirrors 23, 24 of the light deflecting device 16' so that only four deflection producing mirrors are required despite the six-fold folding of the fan. The arrangement of the individual mirrors of the second light deflecting device 19' of the auxiliary module 11 corresponds to the arrangement of mirrors shown in FIG. 6.

In the event that material webs 29 are to be monitored which have a width corresponding only to one half of the material web shown in FIGS. 3 and 4, then it is sufficient to use only the respective main module 10 for the scanning without the auxiliary module 11 being fully operational. In contrast the auxiliary module 11 can only be used in conjunction with the main module 10. Through this modular construction it is possible to prepare optical scanning device with single or double scanning depending on whether the respective main module 10 is to be used with or without the auxiliary module 11.

I claim:

1. Optical scanning device for seeking faults on moving material webs comprising at least one light source; a mirror wheel arranged in a housing which periodically deflects a light beam produced by the light source to generate a scanning beam with which the material web can be scanned transverse to its direction of throughmovement along a scanning line; and at least one light deflecting device arranged after the mirrow wheel which brings about a multiple folding of the scanning beam path out of the plane of the scanning beam, characterised in that the mirror wheel (12) is arranged in the housing (13) with its axis of rotation (14) over one end of the scanning line (21'), with the housing (13) with the optical components arranged therein forming a main scanning module (10); and in that an auxiliary scanning module (11) with a build-on housing (17) is mounted on the housing (13) of the main scanning module (10) at the side associated with the mirror wheel (12), with a second light source and a second light deflecting device (19) being provided in the auxiliary scanning module, wherein the optical components of the additional module (11) are arranged essentially mirror-symmetrically to the optical components of the main module with reference to the mirror wheel (12), so that the end of the scanning line (21') of the main module (10) preferably coincides, somewhat overlapped, with the start of the scanning line (21") of the auxiliary module (11).

2. Scanning device in accordance with claim 1, characterised in that the second light source and/or the second light deflecting device (19) of the auxiliary module (11) are so arranged that the scanning line (21") generated by the corresponding scanning light beam is displaced relative to the scanning line (21') generated by the main module (10) parallel to the scanning direction (A) when the auxiliary module (11) is connected to the main module (10).

3. Scanning apparatus in accordance with claim 2, characterised in that the two scanning lines (21', 21") overlap one another in the scanning direction (A).

4. Scanning apparatus in accordance with claim 1, characterised in that the second light source and the second light deflecting device (19) of the auxiliary module (11) are so arranged that the scanning line (21") generated by the corresponding scanning light beam is aligned with the scanning line (21') generated by the main module (10) when the auxiliary module (11) is connected to the main module (10).

5. Scanning apparatus in accordance with claims 1, characterised in that the light deflecting device (16, 19) in each case includes several plane mirrors (22, 23, 24; 22, 23, 24') of which at least one (23) brings about two foldings of the scanning beam path.

6. Scanning apparatus in accordance with claim 1, characterised in that a scanning objective (25) is arranged in front of each light deflecting device (16, 19).

7. Scanning apparatus in accordance with claim 1, characterised in that the last folding of the respective scanning beam path is brought about by a strip-like concave mirror (26) at the focal point of which the centre of rotation of the fan beam is arranged directly behind the respectively effective facet (12') of the mirror wheel, so that a telecentric scanning beam path is generated.

8. Scanning apparatus in accordance with claim 7, characterised in that a group of correction lenses (27) is provided in front of the respective light deflecting device (16, 19).

9. Scanning apparatus in accordance with claim 1, characterised in that the mirror wheel (12) is so formed, and is so illuminated by the two light sources when the scanning modules (10, 11) are connected together, that the two scanning beams sequentially scan the scanning lines (21', 21"), i.e. "serially" timewise.

10. Scanning apparatus in accordance with claim 1, characterised in that the mirror wheel (12) is so formed, and is so illuminated by the two light sources when the scanning modules (10, 11) are assembled together, that the two scanning beams simultaneously scan the scanning lines (21', 21"), i.e. synchronously and in phase, i.e. in "parallel" timewise.

* * * * *